(12) United States Patent
Kehres et al.

(10) Patent No.: US 8,834,484 B2
(45) Date of Patent: Sep. 16, 2014

(54) SURGICAL INSTRUMENT INCLUDING ANGLE ADJUSTMENT MECHANISM AND QUICK-CONNECT MECHANISM

(75) Inventors: Clint Kehres, Pierceton, IN (US); Daniel Fritzinger, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 262 days.

(21) Appl. No.: 13/295,165

(22) Filed: Nov. 14, 2011

(65) Prior Publication Data

US 2013/0123793 A1 May 16, 2013

(51) Int. Cl.
*A61B 17/58* (2006.01)
*A61B 17/60* (2006.01)
*A61F 2/00* (2006.01)

(52) U.S. Cl.
USPC .............. 606/99; 606/104; 606/279; 606/281

(58) Field of Classification Search
CPC ... A61B 17/80; A61B 17/808; A61B 17/8019
USPC ............................................. 606/91, 99, 104
See application file for complete search history.

(56) References Cited

U.S. PATENT DOCUMENTS

| | | |
|---|---|---|
| 3,702,611 A | 11/1972 | Fishbein |
| 4,504,165 A | 3/1985 | Moeremans |
| 4,565,345 A | 1/1986 | Templeman |
| 4,614,457 A | 9/1986 | Sammon |
| 4,672,964 A | 6/1987 | Dee et al. |
| 4,768,405 A | 9/1988 | Nickipuck |
| 5,055,106 A | 10/1991 | Lundgren |
| 5,489,310 A | 2/1996 | Mikhail |
| 5,499,986 A | 3/1996 | Dimarco |
| 5,746,548 A | 5/1998 | Crandall |
| 6,245,074 B1 | 6/2001 | Allard et al. |
| 6,884,246 B1 | 4/2005 | Sonnabend et al. |
| 6,889,582 B2 | 5/2005 | Wilhelm |
| 7,097,646 B2 | 8/2006 | Schantz |
| 7,220,264 B1 | 5/2007 | Hershberger |
| 7,320,555 B2 | 1/2008 | Chang et al. |
| 7,479,144 B2 | 1/2009 | Myers |
| 7,503,921 B2 | 3/2009 | Berthusen et al. |

(Continued)

OTHER PUBLICATIONS

Depuy Spine, Inc., Skyline Anterior Cervical Plate System, Surgical Technique & Ordering Information, pp. 1-20 (2010).

(Continued)

*Primary Examiner* — Kevin T Truong
*Assistant Examiner* — Samuel Hanna
(74) *Attorney, Agent, or Firm* — Harness, Dickey

(57) ABSTRACT

An instrument assembly can include a handle and an instrument. The handle can include an inner member and an outer member. The inner member can include a rod and a first tip. The outer member can include a second tip and can define a cannulation. The instrument can define a pocket configured to receive the second tip of the outer member. The handle can be adjustable at a desired angle relative to the instrument when the second tip of the outer member is disposed in the pocket and the first tip of the inner member is positioned in the cannulation spaced apart from the second tip. The first tip can be configured to expand the second tip radially outward such that the second tip engages the pocket and locks the handle at the desired angle when the first tip is positioned in the cannulation in engagement with the second tip.

4 Claims, 7 Drawing Sheets

(56) References Cited

U.S. PATENT DOCUMENTS

| | | |
|---|---|---|
| 7,574,768 B2 | 8/2009 | Morris et al. |
| 7,608,076 B2 | 10/2009 | Ezzedine |
| 7,632,276 B2 | 12/2009 | Fishbein |
| 7,722,615 B2 | 5/2010 | Botimer |
| 8,262,708 B2 * | 9/2012 | Michelson .................. 606/280 |
| 8,480,717 B2 * | 7/2013 | Michelson .................. 606/289 |
| 2005/0256578 A1 * | 11/2005 | Blatt et al. ................ 623/17.15 |
| 2006/0095043 A1 * | 5/2006 | Martz et al. .................... 606/90 |
| 2006/0217730 A1 | 9/2006 | Termanini |
| 2006/0241629 A1 | 10/2006 | Krebs et al. |
| 2006/0277811 A1 | 12/2006 | Peterson |
| 2007/0078460 A1 * | 4/2007 | Frigg et al. .................... 606/61 |
| 2007/0225723 A1 | 9/2007 | Berthusen |
| 2009/0138016 A1 | 5/2009 | Berthusen et al. |
| 2009/0173191 A1 | 7/2009 | Davidson et al. |
| 2012/0089192 A1 * | 4/2012 | Biedermann .................. 606/280 |
| 2012/0158058 A1 * | 6/2012 | Michelson .................... 606/246 |

OTHER PUBLICATIONS

DePuy Spine, Skyline Anterior Cervical Plate System Product Catalogue, pp. 1-12 (2009).

DePuy, Anatomic Locked Plating System, Hand Fracture System, Surgical Technique, pp. 1-21 (2009).

DePuy, Skyline Anterior Cervical Plate System, pp. 1-3.

DePuy, The Evolution of Shoulder Care: DePuy Glenoid Solutions, pp. 1-22 (2011).

* cited by examiner

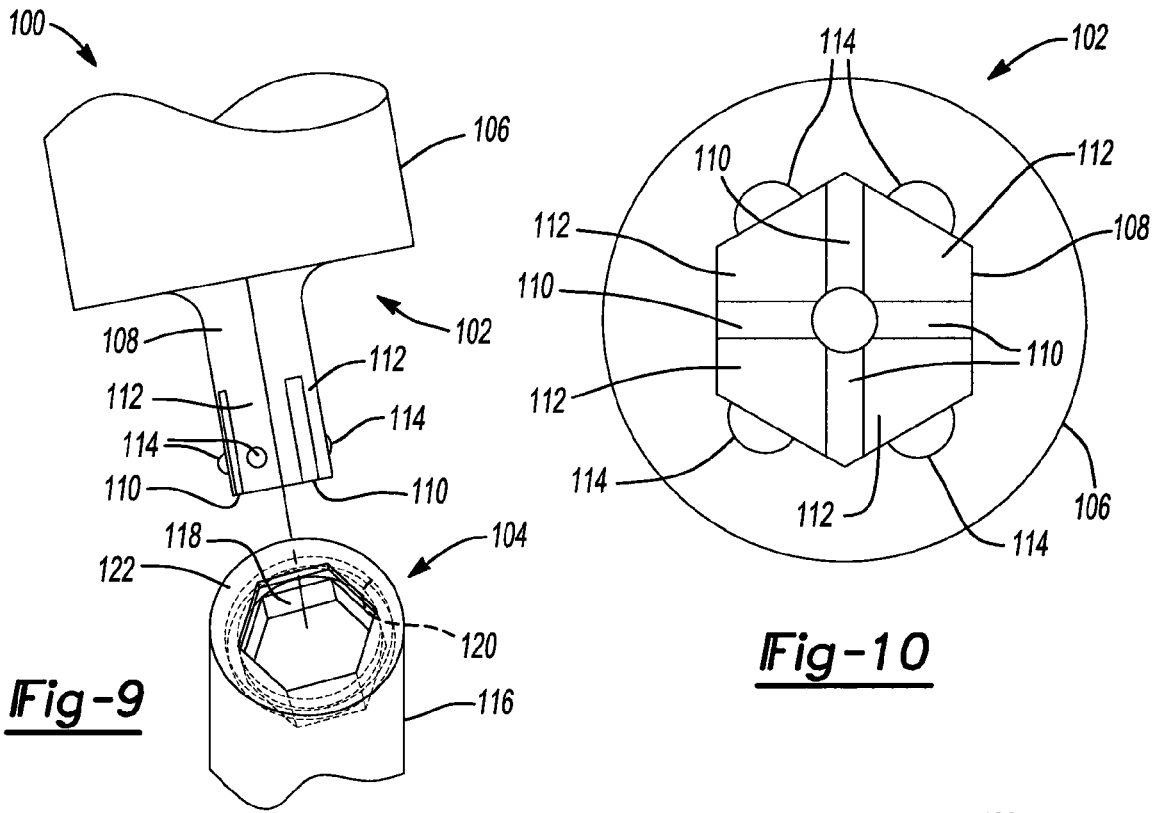
*Fig-9*
*Fig-10*
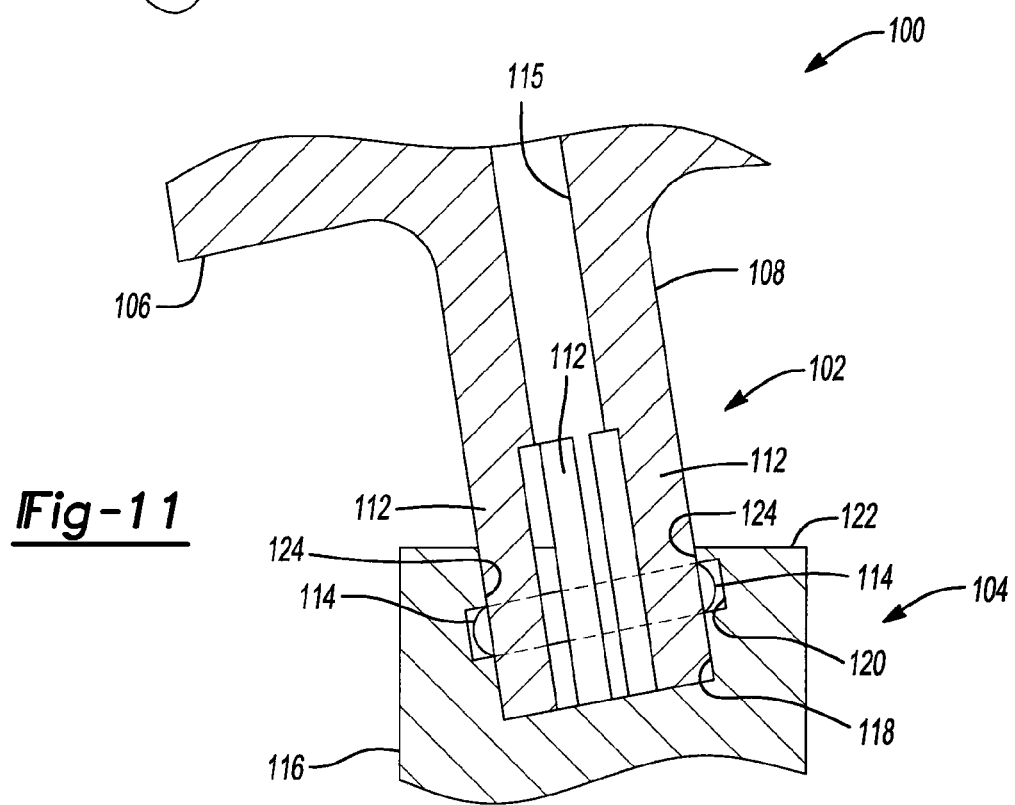
*Fig-11*

SURGICAL INSTRUMENT INCLUDING ANGLE ADJUSTMENT MECHANISM AND QUICK-CONNECT MECHANISM

FIELD

The present disclosure relates to surgical instruments including angle adjustment mechanisms and quick-connect mechanisms.

BACKGROUND

This section provides background information related to the present disclosure which is not necessarily prior art.

Many orthopedic instruments have handles that are fixed at one angle relative to the instruments. Thus, the angle of the handles cannot be adjusted to adapt to a specific anatomy of a patient. As a result, inserting such instruments into a surgical site on the patient can be difficult or impossible.

In addition, many orthopedic instruments have handles that are designed to be threaded onto the instruments. As surgeons can often have bodily or other fluids on their gloves during a surgical procedure, it can be difficult and/or tedious to thread such handles onto the instruments.

SUMMARY

This section provides a general summary of the disclosure, and is not a comprehensive disclosure of its full scope or all of its features.

In one aspect, a variable angle instrument assembly is provided in accordance with the present teachings and can include a handle and an instrument. The handle can include an inner member and an outer member. The inner member can include a rod and a first tip. The outer member can include a second tip and can define a cannulation. The instrument can define a pocket configured to receive the second tip of the outer member. The handle can be adjustable at a desired angle relative to the instrument when the second tip of the outer member is disposed in the pocket and the first tip of the inner member is positioned in the cannulation spaced apart from the second tip. The first tip can be configured to expand the second tip radially outward such that the second tip engages the pocket and locks the handle at the desired angle when the first tip is positioned in the cannulation in engagement with the second tip.

In another aspect, a variable angle instrument assembly is provided in accordance with the present teachings and can include a handle and an instrument. The handle can include an inner member and an outer member. The inner member can include a rod and a tip. The tip can define a first pocket. The outer member can define a cannulation configured to receive the inner member and including a second pocket. The instrument can include a protrusion. The handle can be adjustable at a desired angle relative to the instrument when the protrusion is positioned in the first pocket and the outer member is positioned on the inner member with the second pocket spaced apart from the tip. The outer member can be configured to compress the tip radially inward such that the first pocket engages the protrusion and locks the handle at the desired angle when the second pocket of the outer member engages the tip.

In yet another aspect, a quick-connect instrument assembly is provided in accordance with the present teachings and can include a handle and an instrument. The handle can include a tip including at least one protrusion. The instrument can define a socket and a slot disposed in an outer perimeter of the socket. The tip can be configured to flex radially inward when the protrusion engages the outer perimeter to enable insertion of the tip into the socket. The slot can be configured to engage the at least one protrusion to retain the protrusion in the slot and thereby connect the handle and the instrument. The tip can be configured to flex radially outward when the at least one protrusion engages the slot.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 9 is an exploded isometric view of a portion of a quick-connect instrument assembly according to the present disclosure;

FIG. 10 is an end view of the quick-connect instrument assembly of FIG. 9; and FIG. 11 is a section view of the quick-connect instrument assembly of FIG. 9 taken along line 11-11 shown in FIG. 9.

DETAILED DESCRIPTION

Figure 1:
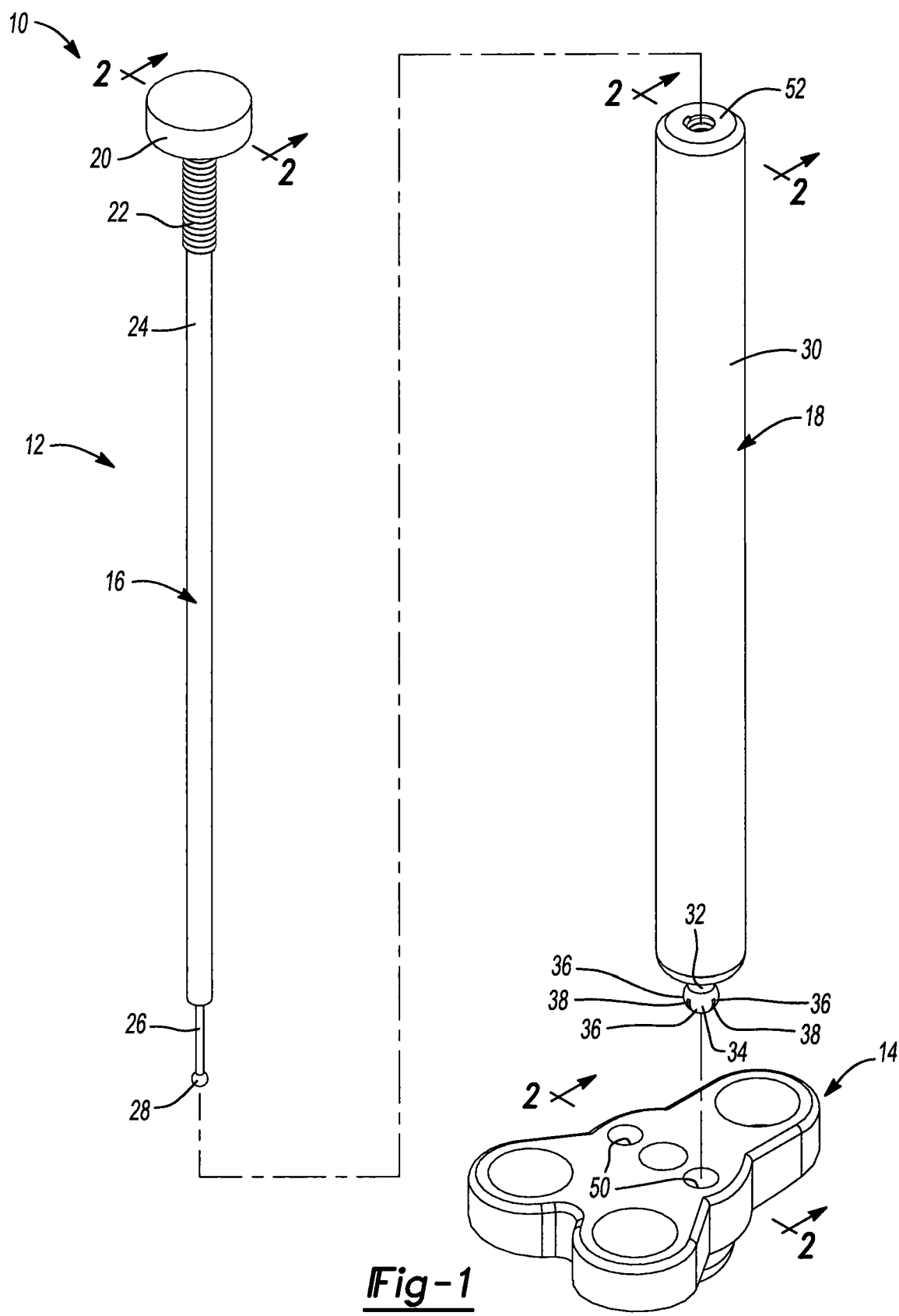
FIG. 1 is an exploded isometric view of a first variable angle instrument assembly according to the present disclosure.

The following description is merely exemplary in nature and is not intended to limit the present disclosure, its application, or uses. It should be understood that throughout the drawings, corresponding reference numerals indicate like or corresponding parts and features with the various elements in each view being drawn to scale. Example embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

Referring now to FIGS. 1 through 4, a variable angle instrument assembly 10 will now be described and can include a handle 12 and an instrument 14. The handle 12 can be positioned at a desired angle relative to the instrument 14 when the handle 12 is disconnected or disengaged from the instrument 14. Once the handle 12 is positioned at the desired angle, the handle 12 is operable to connect to or engage the instrument 14 and thereby lock the handle 12 at the desired angle.

The handle 12 can include an inner member 16 and an outer member 18. The inner member 16 includes a knob 20, outer threads 22, a rod 24, a stem 26, and a tip 28. The tip 28 can be spherical and/or a ball, as shown. The outer member 18 can include a cylindrical member 30, a stem 32, and a tip 34. The tip 34 can be spherical and/or a ball, as shown. In addition, the tip 34 can be slotted, including spherical wings or fingers 36 separated by slots 38.

Figure 2:
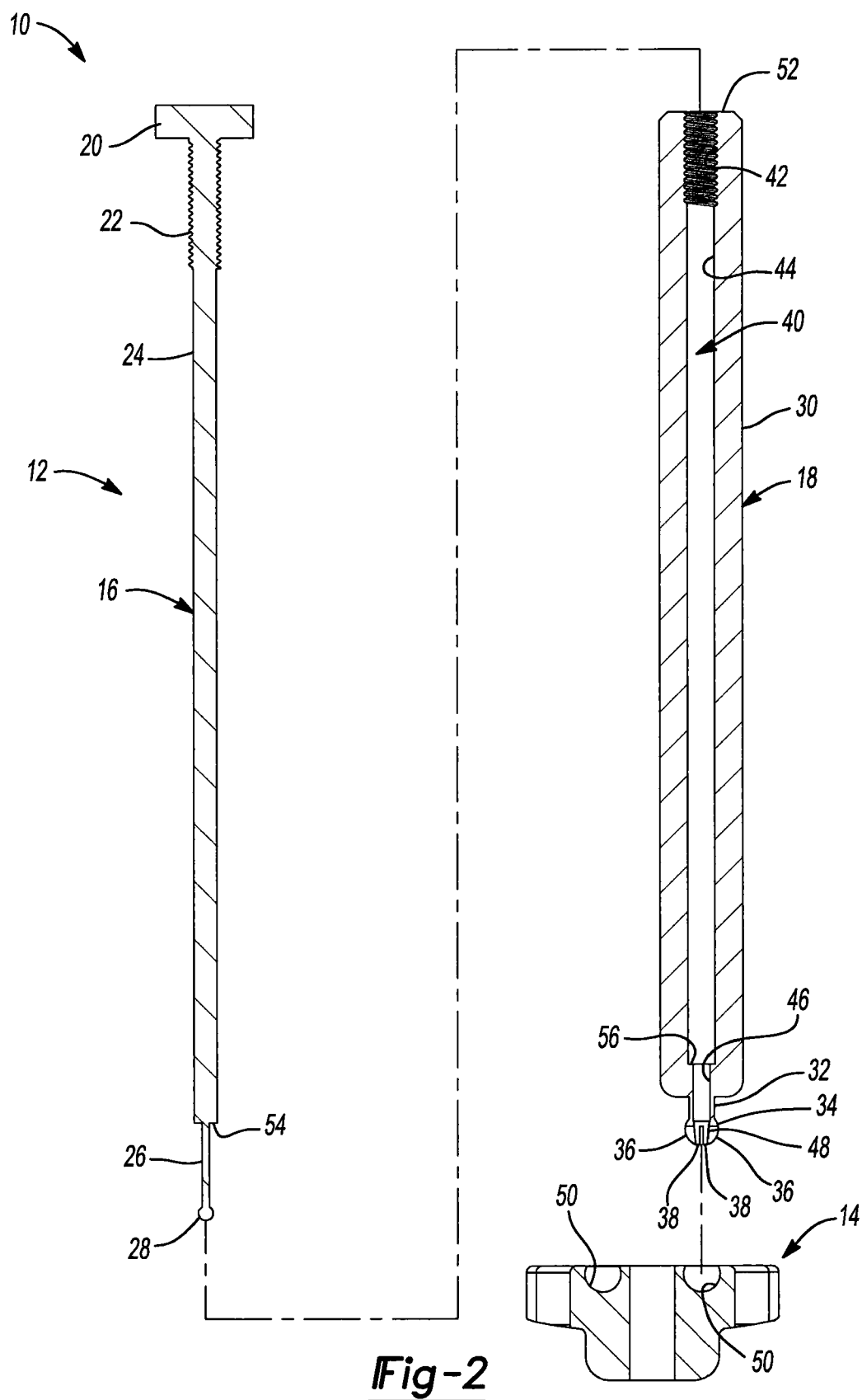
FIG. 2 is a section view of the first variable angle instrument assembly of FIG. 1 taken along lines 2-2 shown in FIG. 1.

The outer member 18 can define a cannulation 40 that extends along the length of the outer member 18, as best shown in FIG. 2. The cannulation 40 can be configured to receive a portion of the inner member 16 that excludes the knob 20. The cannulation 40 can include inner threads 42, a first portion 44, a second portion 46, and a tapered portion 48.

The instrument 14 can be any instrument, such as an orthopedic instrument, and the handle 12 can be used to position the instrument 14 on or within a surgical site. The instrument 14 can define a pocket 50 configured to receive the tip 34 on the handle 12. The pocket 50 can be spherical as shown. It is appreciated that the instrument 14 can be configured differently than shown in FIGS. 1 through 4 without departing from the present disclosure.

Figure 3:
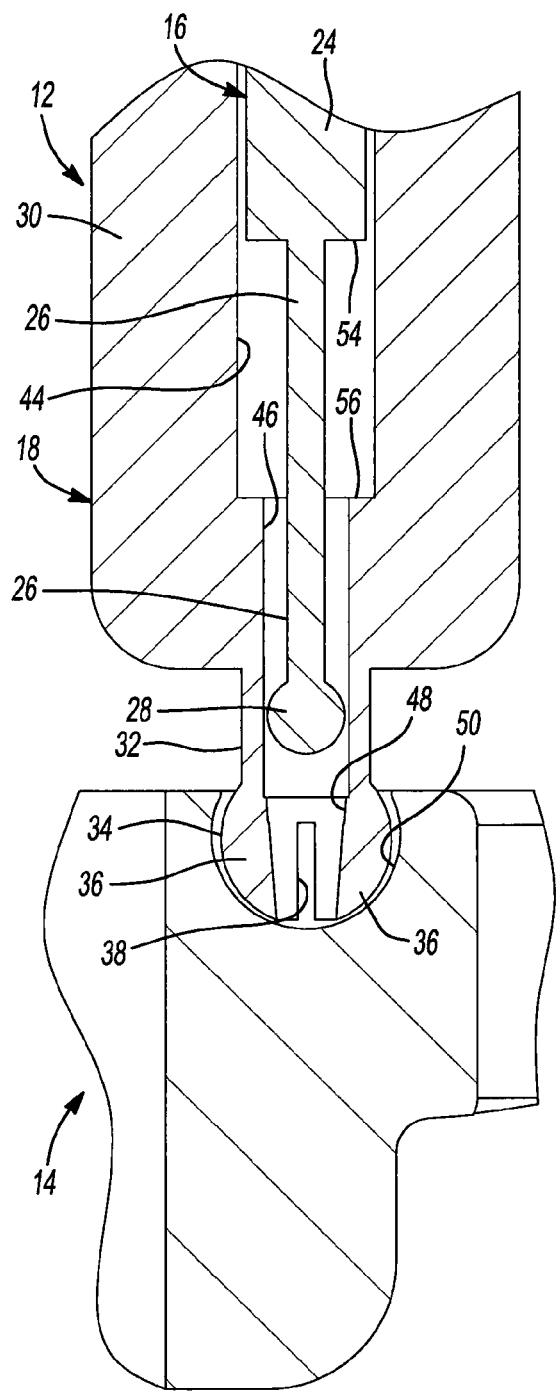
FIG. 3 is an enlarged view of a portion of the section view shown in FIG. 2 depicting an instrument handle disconnected from an instrument.

With continued reference to FIGS. 1 through 4, operation of the variable angle instrument assembly 10 will now be described. Before the handle 12 is connected to the instrument 14, the inner member 16 can be inserted into the cannulation 40 in the outer member 18 such that the inner member 16 is positioned as shown in FIG. 3. In this position, the outer threads 22 on the inner member 16 can engage the inner threads 42 in the outer member 18. In addition, the knob 20 on the inner member 16 can be spaced apart from an end surface 52 (FIG. 2) on the outer member 18. Further, a shoulder 54 on the inner member 16 can be spaced apart from a shoulder 56 on the outer member 18, as shown in FIG. 3.

When the inner member 16 is positioned relative to the outer member 18 as shown in FIG. 3, the tip 34 on the handle 12 can be inserted into the pocket 50 in the instrument 14. The handle 12 can then be positioned at a desired angle relative to the instrument 14. When the handle 12 is positioned at the desired angle, the inner member 16 can be inserted further into the cannulation 40 in the outer member 18 such that the inner member 16 is positioned as shown in FIG. 4.

In this position, the tip 28 on the inner member 16 engages the tapered portion 48 of the cannulation 40. In turn, the fingers 36 on the tip 34 of the outer member 18 expand or flex radially outward and engage the pocket 50 in the instrument 14. This engagement yields a friction fit between the tip 34 of the outer member 18 and the pocket 50 in the instrument 14. The friction fit connects the handle 12 to the instrument 14 and maintains the handle 12 at the desired angle relative to the instrument 14.

Thus, the variable angle instrument assembly 10 includes an expansion mechanism that can be enabled by the engagement between the tapered portion 48 of the cannulation 40 in the outer member 18 and the tip 28 on the inner member 16. The expansion mechanism can also be enabled by the slots 38 in the tip 34 of the outer member 18 that allow fingers 36 of the tip 34 to flex radially outward. The expansion mechanism is not limited to the features shown in FIGS. 1 through 4. For example, the tip 28 on the inner member 16 can be wedged, and the tip 34 on the outer member 18 can be wedged or straight. In addition, the cannulation 40 in the outer member 18 can allow the tip 34 to expand radially outward without defining the slots 38 in the tip 34.

Figure 4:
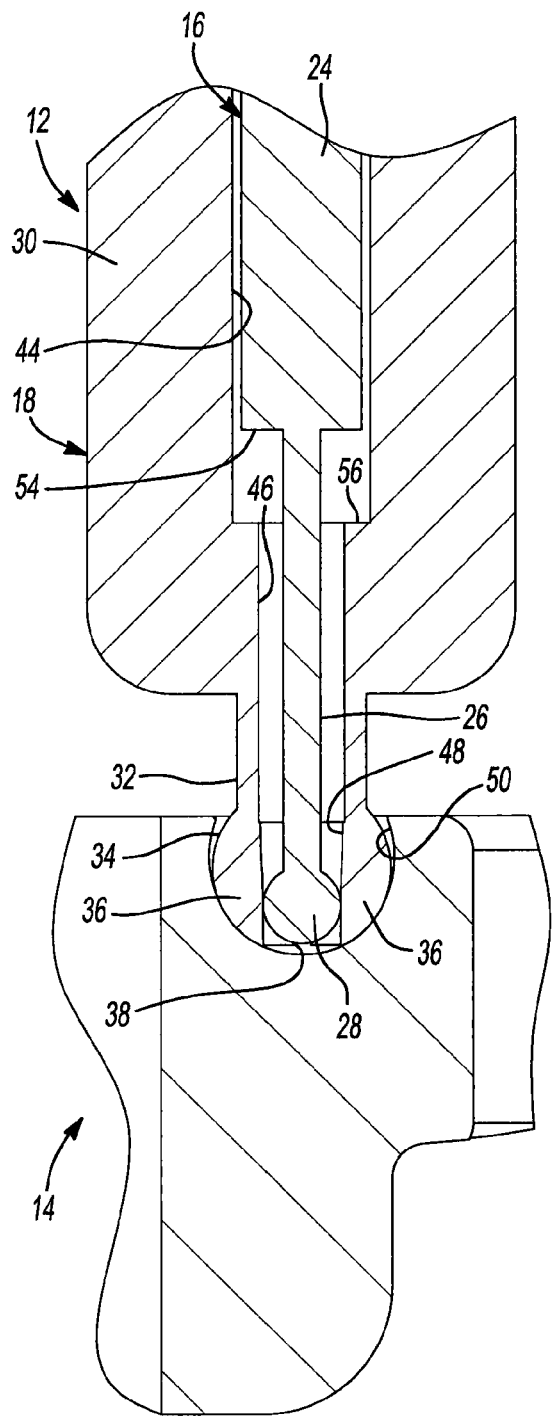
FIG. 4 is an enlarged view of a portion of the section view shown in FIG. 2 depicting an instrument handle connected to an instrument.
Figure 5:
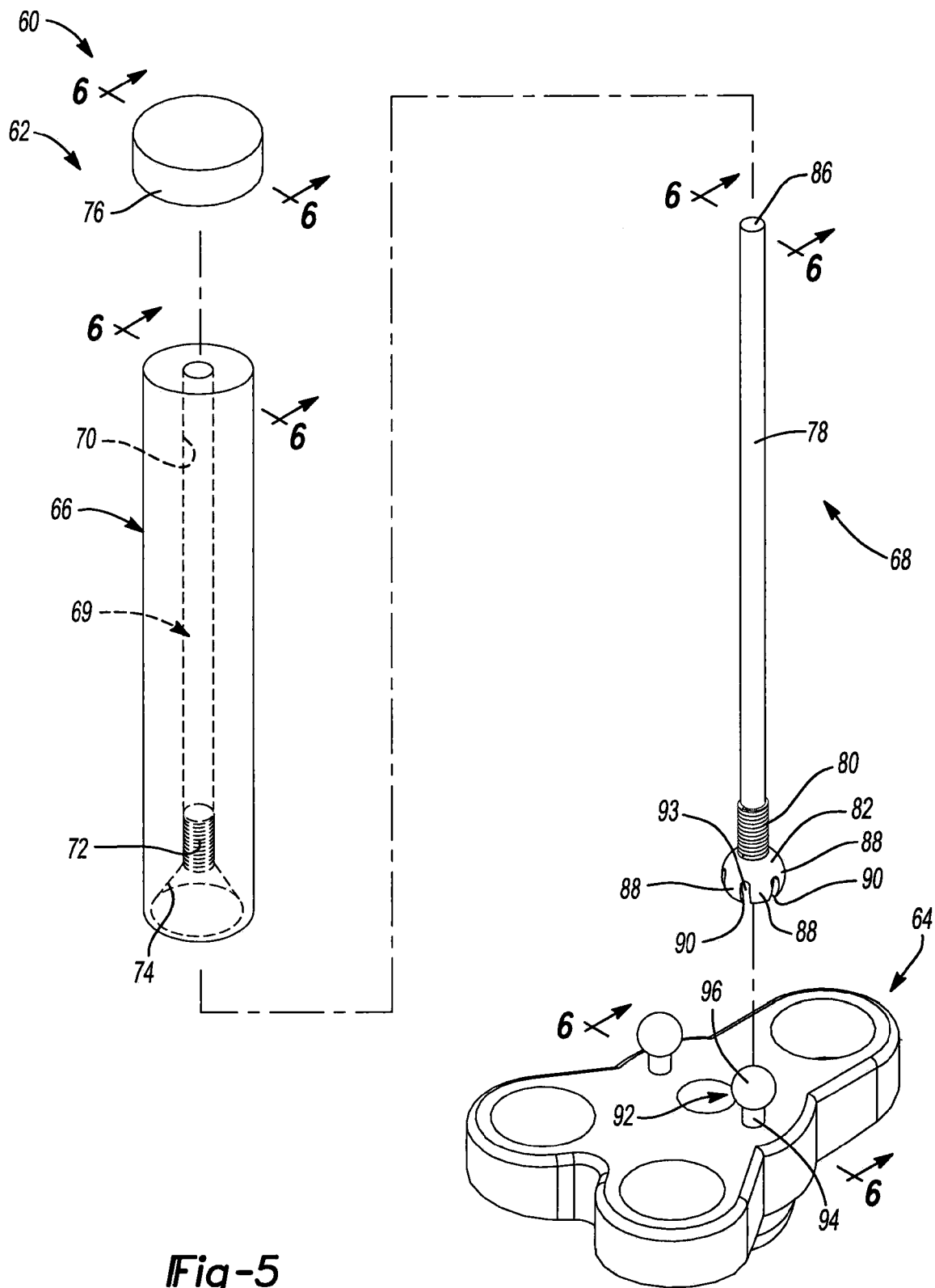
FIG. 5 is an exploded isometric view of a second variable angle instrument assembly according to the present disclosure.

Although FIG. 4 shows the shoulder 54 on the inner member 16 spaced apart from the shoulder 56 on the outer member 18, the shoulder 54 can engage the shoulder 56 when the tip 34 is positioned as shown in FIG. 4. In addition, the outer threads 22 on the inner member 16 can fully engage the inner threads 42 in the outer member 18 such that the outer threads 22 can no longer be threaded into the inner threads 42. Further, the knob 20 on the inner member 16 can engage the end surface 52 on the outer member 18 in the configuration shown in FIG. 4. To reorient the handle 12 relative to the instrument 14 and/or remove the handle 12 from the instrument, the inner member 16 can be returned to the position shown in FIG. 3.

Referring now to FIGS. 5 through 8, a variable angle instrument assembly 60 will now be described and can include a handle 62 and an instrument 64. The handle 62 can be positioned at a desired angle relative to the instrument 64 when the handle 62 is disconnected or disengaged from the instrument 64. Once the handle 62 is positioned at the desired angle, the handle 62 is operable to connect to or engage the instrument 64 and thereby lock the handle 62 at the desired angle.

The handle 62 can include an outer member or collar 66 and an inner member 68. The collar 66 can be cylindrical as shown and can define a cannulation 69 that extends through the collar 66. The cannulation 69 can include a straight portion 70, inner threads 72, and a pocket 74. The pocket 74 can be conical as shown.

Figure 6:
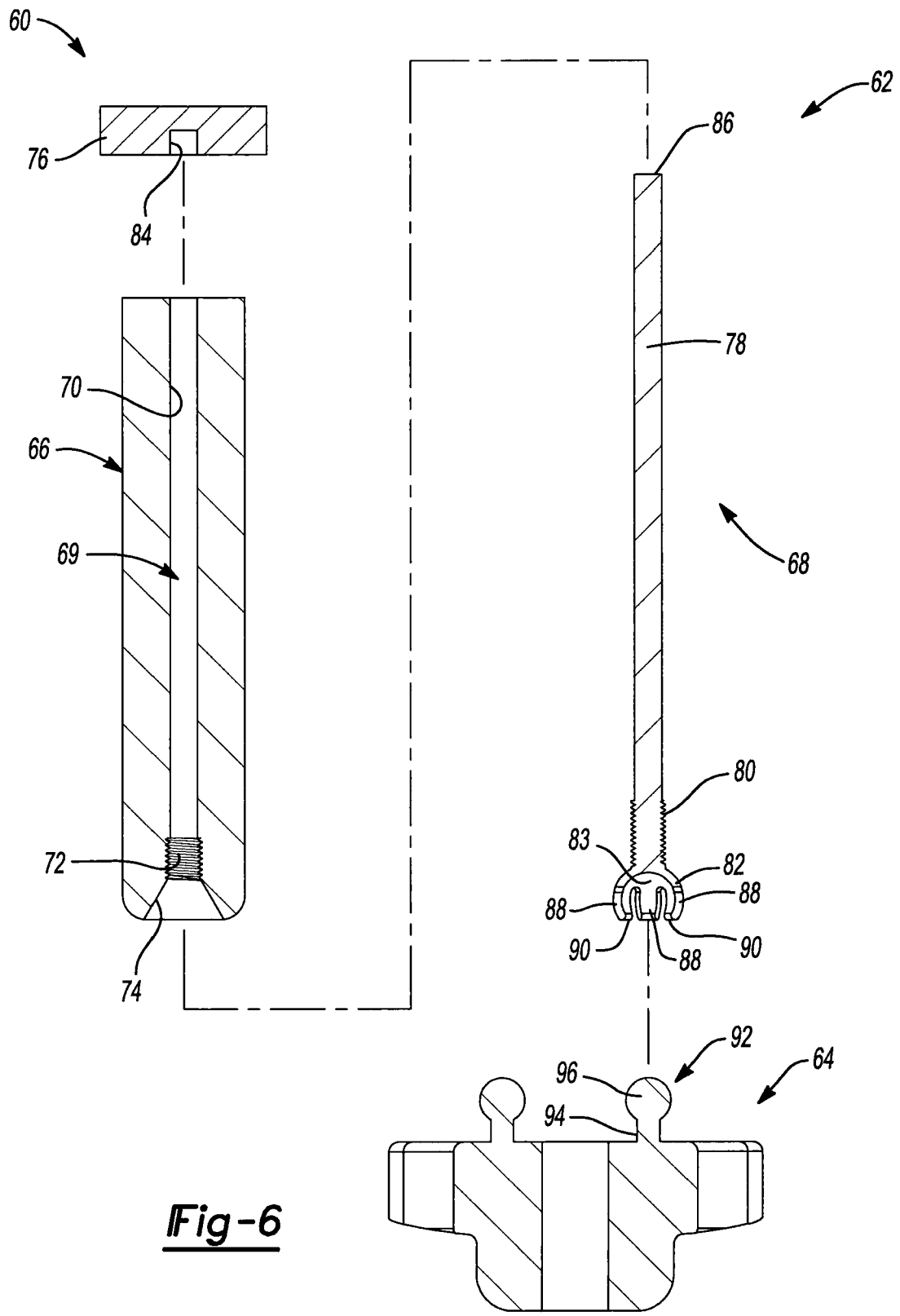
FIG. 6 is a section view of the second variable angle instrument assembly of FIG. 5 taken along lines 6-6 shown in FIG. 5.

The inner member 68 can include a knob 76, a rod 78, outer threads 80, and a tip 82 defining a pocket 83 therein. The tip 82 and/or the pocket 83 can be spherical, as shown. The knob 76 can define a cavity 84 configured to receive an end 86 of the rod 78, as best shown in FIG. 6. The collar 66 can be slid over the rod 78, the end 86 of the rod 78 can be inserted into the cavity 84 in the knob 76. The knob 76 can also be fixed (e.g., welded) to the end 86 of the rod 78. Thus, the collar 66 can be captured between the knob 76 and the tip 82. The tip 82 can include fingers 88 separated by slots 90. The fingers 88 can be spherical, as shown.

The instrument 64 can be any instrument, such as an orthopedic instrument, and the handle 62 can be used to position the instrument 64 on or within a surgical site. The instrument 64 can include a protrusion 92 including a stem 94 and a spherical member or ball 96. It is appreciated that the instrument 64 can be configured differently than shown in FIGS. 5 through 8 without departing from the present disclosure.

Figure 7:
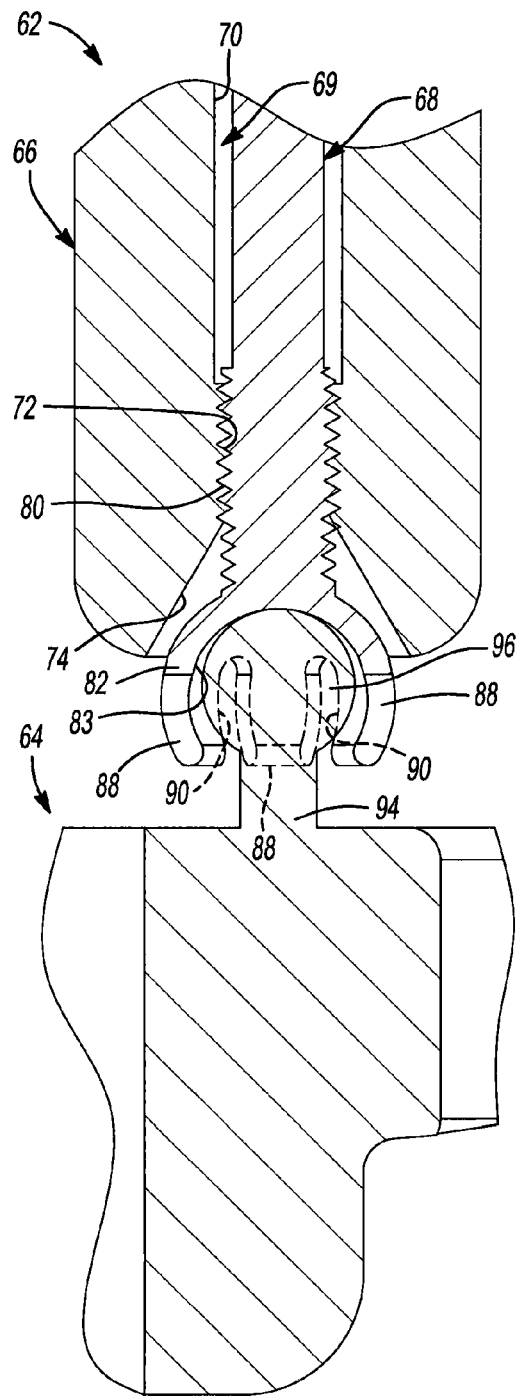
FIG. 7 is an enlarged view of a portion of the section view shown in FIG. 6 depicting an instrument handle disconnected from an instrument.

With continued reference to FIGS. 5 through 8, operation of the variable angle instrument assembly 60 will now be described. Before the handle 62 is connected to the instrument 64, the inner threads 72 in the collar 66 can be threaded onto the outer threads 80 on the inner member 68 such that the collar 66 is positioned as shown in FIG. 7. In this position, the pocket 74 of the collar 66 can be spaced apart from the tip 82.

Figure 8:
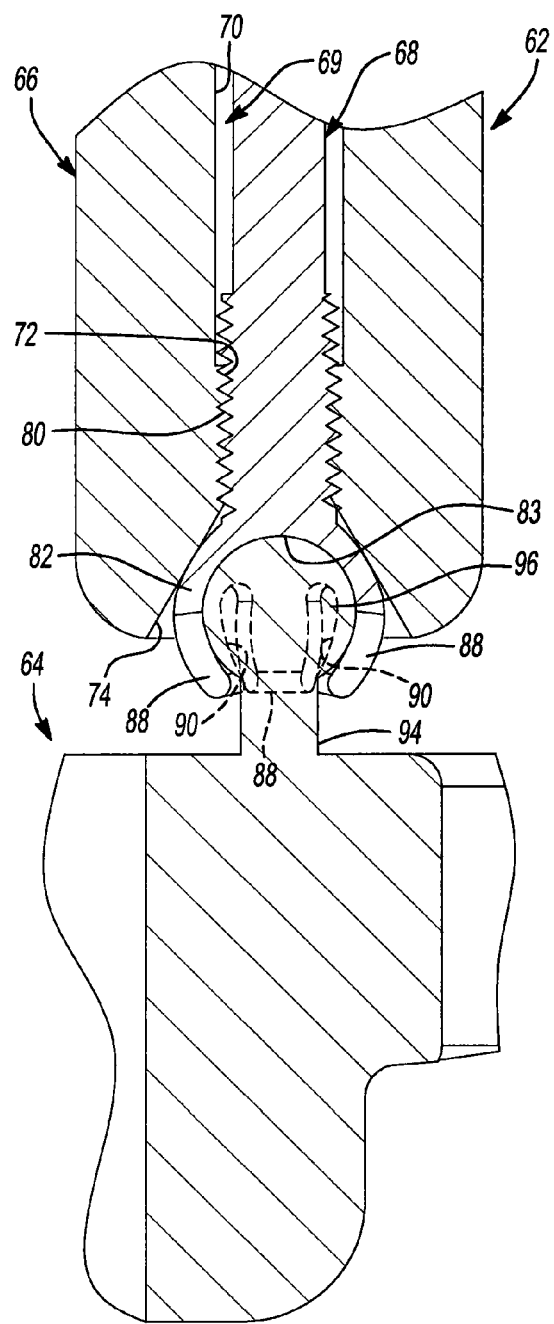
FIG. 8 is an enlarged view of a portion of the section view shown in FIG. 6 depicting an instrument handle connected to an instrument.

When the collar 66 is positioned relative to the inner member 68 as shown in FIG. 7, the pocket 83 in the inner member 68 can be placed over the ball 96 on the instrument 64, as shown in FIGS. 7 and 8. The handle 62 can then be positioned at a desired angle relative to the instrument 64. When the handle 62 is positioned at the desired angle, the collar 66 can then be threaded further onto the inner member 68 such that the collar 66 is positioned relative to the inner member 68 as shown in FIG. 8.

In this position, the pocket 74 of collar 66 engages the outer surface of the tip 82. In turn, the fingers 88 on the tip 82 of the inner member 68 are compressed radially inward, causing the pocket 83 in the handle 12 to engage the ball 96 on the instrument 64. This engagement yields a friction fit between the ball 96 on the instrument 64 and the pocket 83 in the handle 12. The friction fit connects the handle 62 to the instrument 64 and maintains the handle 62 at the desired angle relative to the instrument 64. To reorient the handle 62 relative to the instrument 64 and/or detach the handle 62 from the instrument, the collar 66 can be returned to the position shown in FIG. 7.

Thus, the variable angle instrument assembly 60 includes a compression mechanism that can be enabled by the engagement between the pocket 74 of the collar 66 and the outer surface of the tip 82. In addition, the compression mechanism can be enabled by the slots 90 in the tip 82, which allow the tip 82 to flex radially inward. The compression mechanism is not limited to the features shown in FIGS. 5 through 8. For example, the tip 82 on the inner member 68 can be wedged, and the pocket 74 in the collar 66 can be cylindrical. In addition, inner member 68 can be cannulated to allow the tip 82 to flex radially outward without defining the slots 90 in the tip 82.

Further, although the variable angle instrument assemblies 10, 60 include inner and outer members that are coupled using threads, the inner and outer members can be coupled together in other ways. For example, one of the inner and outer members can define a slot and the other one of the inner and outer members can include a pin that slidably engages the slot. In addition, the end of the pin can be larger than the width of the slot to retain the pin in the slot.

Referring now to FIGS. 9 through 11, a quick-connect instrument assembly 100 will now be described and can include a handle 102 and an instrument 104. The handle 102 can include a cylindrical member 106 and a tip 108. The tip 108 can be hexagonal, as best shown in FIG. 10, or have another non-circular shape. The tip 108 can be slotted. Thus, the tip 108 can define slots 110 that separate wings or fingers 112 of the tip 108.

The slots 110 allow the fingers 112 of the tip 108 to flex radially inward and outward. Protrusions 114 can be disposed on the outer surface of the fingers 112. The protrusions 114 can be hemispherical, as shown, and can be formed integrally with the fingers 112. The handle 102 can define a cannulation 115 that extends along the length of the handle 102, as shown in FIG. 11.

The instrument 104 includes a cylindrical member 116 defining a socket 118 and a cutout or slot 120, as best shown in FIG. 11. The socket 118 is configured to receive and/or conform to the tip 108. For example, the socket 118 can be hexagonal, as shown. The socket 118 can be oriented at an oblique angle relative to an end 122 of the cylindrical member 116, as shown. The slot 120 can be annular or circular, extending around the perimeter of the socket 118. The slot 120 can have a rectangular cross section, as shown in FIG. 11.

With continued reference to FIGS. 9 through 11, operation of the quick-connect instrument assembly 100 will now be described. Before connecting the handle 102 into the instrument 104, the handle 102 can be positioned adjacent to the instrument 104 and roughly aligned with the socket 118 in the instrument 104, as shown in FIG. 9. The tip 108 of the handle 102 can then be inserted into the socket 118 of the instrument 104 to connect the handle 102 to the instrument 104.

When the tip 108 initially enters the socket 118, the protrusions 114 on the tip 108 engage surfaces 124 in the socket 118, forcing the fingers 112 radially inward and compressing the tip 108. The slots 110 in the tip 108 enable the tip 108 to flex radially inward so that the tip 108 can be inserted into the socket 118. When the tip 108 is positioned as shown in FIG. 11, the fingers 112 are no longer held radially inward and the protrusions 114 snap into the slot 120 in the socket 118 such that the handle 102 is connected to the instrument 104. In this position, the engagement between the protrusions 114 and the socket 118 retains the tip 108 within the socket 118. To disconnect the handle 102 from the instrument 104, the handle 102 can be pulled with a force that is sufficient to overcome the engagement between the protrusions 114 and the socket 118.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A variable angle instrument assembly, comprising:
a handle including an inner member and an outer member, the inner member including a rod and a first tip, the outer member including a cylindrical member and a spherical second tip and defining a cannulation extending in a direction from a proximal end of the outer member to a distal end of the outer member, the cannulation including a shoulder and a tapered portion disposed within the second tip and extending to a distalmost end of the outer member, wherein the inner member includes outer threads and the outer member includes inner threads configured to mesh with the outer threads on the inner member; and
an instrument defining a pocket configured to receive the spherical second tip of the outer member, the handle being adjustable at a desired angle relative to the instrument when the spherical second tip of the outer member is disposed in the pocket and the first tip of the inner member is positioned in the cannulation spaced apart from the spherical second tip, wherein the first tip expands the spherical second tip radially outward without engaging the pocket such that the spherical second tip engages the pocket and locks the handle at the desired angle when the first tip is positioned in the cannulation in engagement with the spherical second tip, and wherein the engagement between the first tip and the second tip occurs inside the pocket.

2. The variable angle instrument assembly of claim 1, wherein the spherical second tip of the outer member is slotted.

3. The variable angle instrument assembly of claim 1, wherein the first tip of the inner member is spherical.

4. The variable angle instrument assembly of claim 1, wherein the pocket in the instrument is spherical.

* * * * *